United States Patent [19]

Azzoni et al.

[11] Patent Number: 5,759,796
[45] Date of Patent: Jun. 2, 1998

[54] METHOD FOR THE DETERMINATION OF LACTIC ACID IN ORGANIC MATERIALS OF ALIMENTARY INTEREST AND BIOSENSOR FOR PUTTING THIS METHOD INTO EFFECT

[75] Inventors: Alfredo Azzoni; Corrado Belicchi; Barbara Cavalieri, all of Parma; Franco Mazzei; Claudio Botre', both of Rome, all of Italy

[73] Assignee: CO.RI.AL. S.C.P.A., Foggia, Italy

[21] Appl. No.: 647,340

[22] Filed: May 9, 1996

[51] Int. Cl.⁶ .............. C12Q 1/28; C12Q 1/26; C12Q 1/00
[52] U.S. Cl. .............. 435/28; 435/25; 435/26; 435/4; 435/14; 435/817; 435/287.1; 435/287.5; 562/589; 204/403; 204/297
[58] Field of Search .............. 435/28, 25, 26, 435/4, 14, 817, 287, 288, 291, 287.1, 287.5; 204/403, 297; 562/589

[56] References Cited

U.S. PATENT DOCUMENTS 4,166,763  9/1979  Esders et al. .............. 435/28
4,237,222  12/1980 Misaki et al. .............. 435/25
4,592,996  6/1986  Yamanishi et al. .............. 435/28

OTHER PUBLICATIONS

Cheng et al, Clinica Chimica Acta, vol. 91, pp. 295–301, (1979). Month not available.

*Primary Examiner*—Louise Leary
*Attorney, Agent, or Firm*—Morgan & Finnegan, L.L.P.

[57] ABSTRACT

A method is described for the determination of lactic acid in organic materials of alimentary interest that involves reacting, in a buffered aqueous medium, a sample of the said materials, or a solution obtained by extracting them, with an enzyme system comprising L(+) lactate oxidase, D(−) lactate dehydrogenase and horseradish peroxidase and measuring the concentration of any oxygen produced as a result of the oxidation of the lactic acid contained in the said sample with an amperometric electrode that is selective for oxygen.

A biosensor that can be used to put the above method into effect is also described.

8 Claims, 3 Drawing Sheets

METHOD FOR THE DETERMINATION OF LACTIC ACID IN ORGANIC MATERIALS OF ALIMENTARY INTEREST AND BIOSENSOR FOR PUTTING THIS METHOD INTO EFFECT

TECHNICAL FIELD

In general terms, the present invention relates to the detection and determination of lactic acid in organic materials of alimentary interest.

In particular, the present invention relates to an enzymatic method for the simultaneous determination of L(+) lactic acid and D(−) lactic acid in organic materials of industrial interest in the agroalimentary field.

The invention also relates to a biosensor that can be used to put the above method into effect.

BACKGROUND OF THE INVENTION

It is well known that many organic materials of alimentary interest undergo degradation processes, most of which are caused by microorganisms of various types, not necessarily pathogenic, that are present in the environment.

These degradation processes can result in the formation of lactic acid in an optically active form.

In particular, when the degradation is caused by microorganisms and algae, D(−) lactic acid is generally formed; however, there are microorganisms, such as the lactobacilli, that cause the formation of both enantiomers of lactic acid in a racemic mixture.

The level of lactic acid present in food substances can therefore be used an indicator of the freshness and quality of these substances.

In particular, the D(−) enantiomer of lactic acid is an indicator of the reduced freshness of vacuum-packed or prepacked meat-based products, while the racemic mixture is an indicator of bacterial contamination of foods of plant origin, such as the juice and flesh of tomatoes or other types of vegetables or fruit.

When the concentration of lactic acid in these foods reaches values in the region of 300 mg/kg, the bacterial contamination will already have reached levels that will alter the organoleptic properties of the foods.

The concentration of lactic acid within food matrices can be determined by various classical methods of chemical and instrumental analysis that are highly sensitive and provide extremely accurate results; however, these have the disadvantage that they require very expensive equipment and must be performed by specially trained staff. In addition, these tests can only be performed in chemical laboratories and are unsuitable for use at the place of sampling. All this gives rise to high operating costs and the use of these tests is therefore necessarily limited to a small number of samples.

Finally, the time required to perform an analysis by the methods described above is fairly lengthy, generally of the order of several hours, since laborious preparation procedures and pretreatment of the samples are necessary.

Recently, various analytical methods based on the use of enzymes have been developed.

These methods are generally based on monoenzyme systems; some of them use enzymes that catalyse the oxidation of L(+) lactic acid (see, for example, M. Mascini et al. (1987) "Lactic acid and pyruvate electrochemical biosensors for whole blood in ex vivo experiments with an endocrine artificial pancreas", Clin. Chem., 33, 591–593, and F. Mizutani et al. (1985) "An Enzyme Electrode for L-lactic acid with a Chemically Amplified Response", Anal. Chim. Acta, 177, 153–166), while others are based on determination of the concentration of the NADH that is formed at the same time as pyruvic acid as a result of the oxidation of lactic acid (see, for example, H. Durliat, M. Comtat (1980), "Adsorption of L(+) Lactic acid Dehydrogenase from Aerobic Yeast on a Platinum Electrode", J. Electoanal. Chem. Interfacial. Electrochem., 89, 221–229; H. Durliat et al. (1990) "Bienzyme Amperometric Lactic Acid-Specific Electrode", Anal. Chim. Acta, 231, 309–311; L. Gorton, A. Hedlund (1988), "A flow-injection method for the amperometric determination of L-lactic acid with immobilized enzymes and a chemically modified electrode", Anal. Chim. Acta, 213, 91–100).

The above methods permit the determination of both enantiomers of lactic acid and involve the use of D(−) and L(+) lactate dehydrogenase, which, in the presence of the coenzyme NAD, cause oxidation of the lactate to pyruvate and simultaneous reduction of the NAD to NADH. The concentration of lactic acid in the food matrix is deduced from the concentration of NADH.

The NADH is in turn determined by means of its direct oxidation on a solid electrode surface, generally made of platinum or graphite (cf. J. Moiroux, P. J. Elving (1979), "Optimization of the analytical oxidation of dihydronicotinamide Adenine Dinucleotide at carbon and platinum electrodes", Anal. Chem., 51, 346–350).

However, this method has various disadvantages due to the large difference in discharge potential (+800 mV) involved; under these conditions it is possible for foreign substances that could interfere with the measurement to be discharged at the electrode.

As an alternative, it has been suggested that NADH could be determined by reacting it with hexacyanoferrate(III) in the presence of the enzyme diaphorase to obtain hexacyanoferrate(II), the concentration of which can be determined amperometrically by its discharge at a platinum electrode with a potential of +400 mV by comparison with a suitable reference electrode, generally Ag/AgCl (M. Montagné, H. Durliat, M. Comtat (1993) "Simultaneous use of dehydrogenases and hexacyanoferrate(III) ion in electrochemical biosensors for L-lactic acid, D-lactic acid and L-glutamate ions", Anal. Chim. Acta, 278, 25–33).

Even this last method is not entirely satisfactory because of its complexity and laboriousness.

SUMMARY OF THE INVENTION

The problem that led to the development of the present invention was the need to provide a method for the determination of both enantiomers of lactic acid present in organic materials of alimentary interest that overcomes the disadvantages of the known methods based on the separate determination of the two enantiomers, that is simple to perform, even for staff who are not specially trained, and that may also be suitable for use "in the field", i.e. in the place where the organic materials to be analysed are located.

This problem has been solved by a method comprising the following stages:

reacting, in a buffered aqueous medium, a sample of organic material of alimentary interest, or a solution obtained by extracting the said material with solvent, with an enzyme system comprising L(+) lactate oxidase (LOD), D(−) lactate dehydrogenase (D-LDH) and horseradish peroxidase (HPO) in the presence of NAD and $Mn^{++}$, measuring the concentration of any oxygen given off as a result of the oxidation of the lactic acid contained in the sample or the solution with the aid of an amperometric electrode that is selective for oxygen.

The enzymes LOD, D-LDH and HPO are preferably immobilized on at least one suitable support.

Advantageously, these enzymes can be immobilized on a single support comprising a membrane.

According to a preferred embodiment of the method according to the invention, the amperometric electrode used for the measurement is separated from the buffered aqueous medium by a first, gas-permeable membrane that is in direct contact with the electrode; a second membrane bearing the abovementioned immobilized enzymes is then placed externally over the first membrane.

Advantageously, the above first membrane is made of Teflon.

A further membrane, comprising a dialysis membrane, is preferably placed externally over the above second membrane.

The above second membrane preferably consists of a membrane made of nylon 6,6 bearing carboxyl groups on its surface.

The solvents that can be used to extract the lactic acid from the organic materials of alimentary interest are water and polar solvents miscible with water.

The pH of the buffered aqueous medium is preferably in the range 8.0 to 8.5.

The concentration of NAD is preferably between 1 and 2 mM and that of $Mn^{++}$ between 1 and 2 mM.

The above amperometric electrodes attached to membranes bearing enzyme systems belong to the class of "biosensors".

BRIEF DESCRIPTION OF THE DRAWINGS

The method according to the invention will now be described in greater detail, with reference to the attached drawings in which.

DETAILED DESCRIPTION OF THE INVENTION

Figure 1:
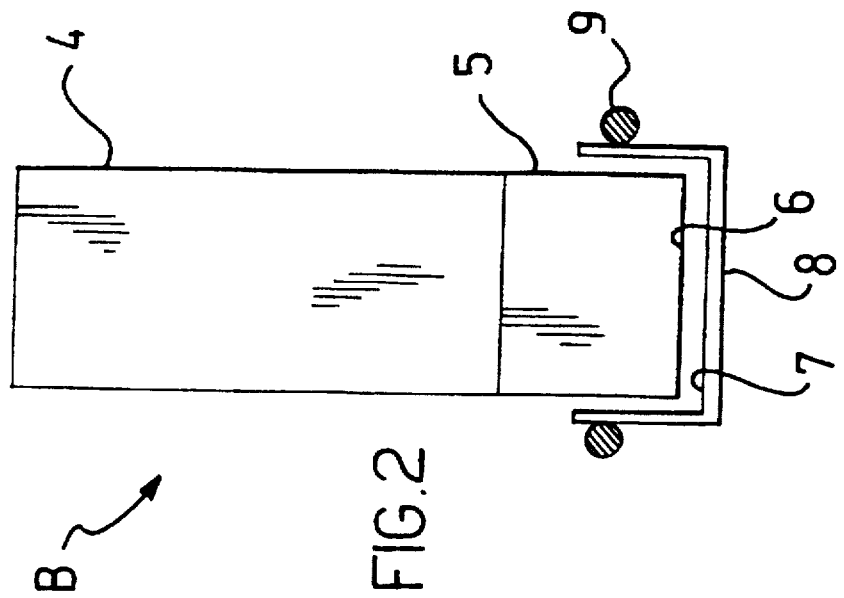
FIG. 1 shows a diagrammatic representation of the amperometric electrode of the electrochemical biosensor.

With reference to FIG. 1, an amperometric electrode for putting the method according to the invention into effect comprises a commercial sensor 1 for oxygen, consisting, for example, of a platinum wire electrode 2 coated with a layer 2a of an epoxy resin, which separates and insulates it from a reference electrode 3 (Ag/AgCl) arranged coaxially around it. The electrodes 2 and 3 are fixed inside a cylindrical container 4 filled with an electrolyte solution or an electrolyte gel, with a suitable coating 3a interposed. However, one end of the platinum electrode 2 is exposed to enable it to act as an indicator electrode for the oxygen present in the buffered aqueous medium. This electrode 2 is kept at a potential of approximately −650 mV compared with the reference electrode 3. A cap 5, also cylindrical, screws onto the cylindrical container 4 over the exposed end of the platinum electrode 2. The base of this cylindrical cap 5 consists of a gas-permeable membrane 6, generally made of Teflon.

Figure 2:
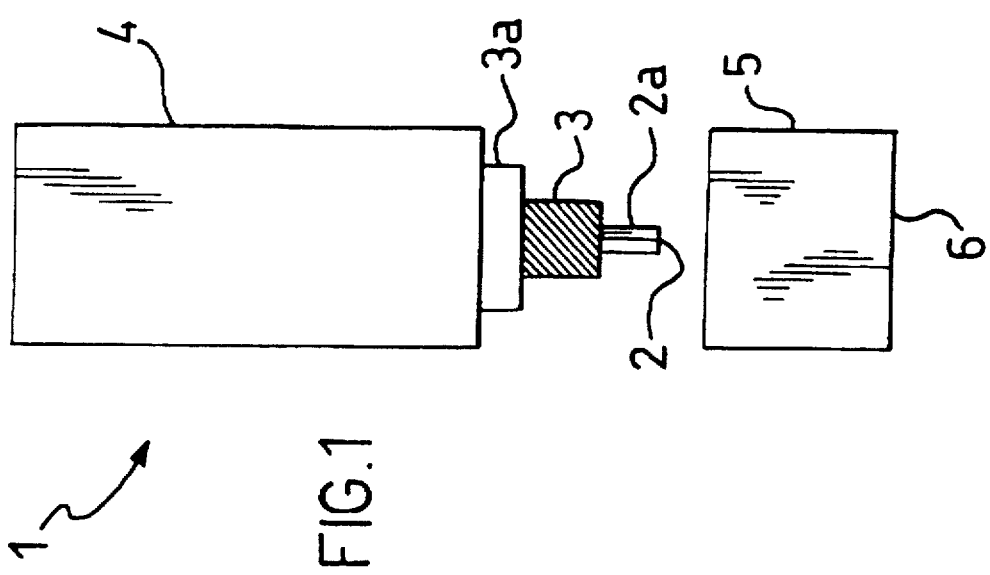
FIG. 2 shows a diagrammatic representation of the elec-trochemica biosensor.

With reference to FIG. 2, a membrane 7, on which are immobilized L(+)lactate oxidase (LOD), D(−) lactate dehydrogenase (D-LDH) and horseradish peroxidase (HPO), and a dialysis membrane 8 are placed in that order over the membrane 6 of a biosensor B according to the invention. The membranes 7 and 8 are held firmly in place by means of an elastic ring 9.

Figure 3:
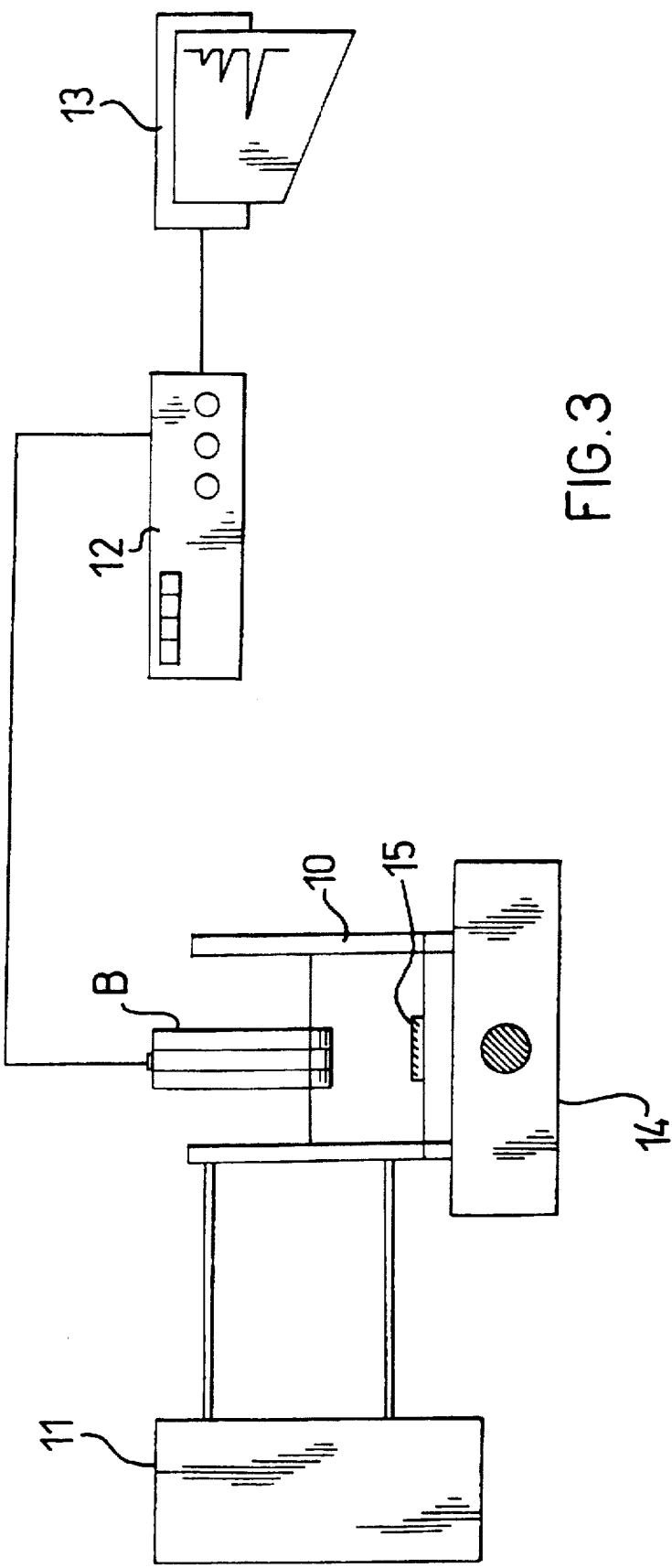
FIG. 3 shows a diagrammatic representation of equipment for putting he method according to the invention into effect.

With reference to FIG. 3, the above biosensor B is inserted into a cell 10 that is kept at a constant temperature by a thermostat 11 and contains a buffered aqueous solution at pH 8.0–8.5, in which the biosensor B is partially immersed; the latter is connected to an amperometric measuring device 12, whose output is connected to a chart recorder 13 or to any other data recording system.

Advantageously, the cell 10 is positioned on a magnetic stirrer 14 and provided with the relevant magnetic bar 15.

The method according to the invention will be further described with reference to an example that does not limit the scope of the invention and is provided purely by way of illustration.

EXAMPLE

A sample of tomato juice was tested for its lactic acid content by the method according to the invention using the equipment shown diagrammatically in FIG. 3.

The membrane 7 of the biosensor containing immobilized LOD, D-LDH and HPO had been prepared as follows:

A uniform layer of 0.25 mg of lactate oxidase (20 U/mg of solid from *Pediococcus sp.*), 0.5 mg of D(−) lactate dehydrogenase (10 U/mg of solid from *Staphylococcus epidermidis*) and 0.25 mg of horseradish peroxidase (300 U/mg of solid from *Armoracia rusticana*), dissolved in 20 μl of a 12% solution of polyazetidine prepolymer (P.A.P.) in water, was applied to a Biodyne Transfer membrane made of nylon 6,6 with a diameter of 8 mm and a pore size of 0.2 mm, functionalized with carboxyl groups.

After 24 hours at 4° C., the membrane was washed with 0.1M phosphate buffer at pH 7.00 and then stored in the dry at 4° C.

The multienzymatic biosensor for the determination of lactic acid was then prepared by placing over the teflon membrane 6 of the oxygen sensor, in the following order, the membrane 7 prepared as described above and a dialysis membrane 8, the above membranes then being fixed to the sensor with the aid of an elastic ring 9.

The prepared biosensor was immersed in the cell 10 thermostatically maintained at 37° C. described earlier, which contained 4.5 ml of buffer comprising 0.1M glycine, pH 8.0, and 0.5 ml of 2.0 mM NAD+$Mn^{++}$, and connected to the amperometric measuring device 12.

A sample of 0.1 ml of tomato juice that had been filtered on filter paper was added to the buffered solution in the thermostatically-controlled cell 10, which was stirred with the magnetic stirrer 14.

The change in current intensity registered after the addition of the test sample was proportional to the concentration of oxygen, which in turn is proportional to the amount of D(−) and L(+) lactic acid in the sample.

This amount could be quantified with reference to a calibration curve obtained beforehand with standard solutions of lactic acid containing 90 or 180 ppm of lactic acid.

In the case in question, a total quantity of lactic acid (D(−) and L(+) enantiomeric forms) equivalent to 58.5 ppm was found (mean of ten determinations).

An aliquot of the same sample of tomato juice was analyzed by the enzymatic spectrophotometric method based on the Boehringer-Mannheim Enzymatic Kit, Cat. No. 1112821, to determine its total lactic acid content (D(−)+L(+)).

The results of this analysis show that the lactic acid content was 59.4 ppm.

This confirms the reliability of the method according to the present invention.

The procedure described above was repeated with another 9 samples of tomato juice from different sources. The results obtained are summarized in Table I below (values expressed in ppm), which also gives the results of the analyses performed on the same samples by the enzymatic spectrophotometric method described above.

TABLE I

| Sample No. | Values obtained by the method acc. to the invention (a) | Values obtained by the enzymatic spectrophotometric method, Boehringer-Mannheim Enzymatic Kit Cat. No. 1112821 (b) | (a − b)/b% |
|---|---|---|---|
| 1 | 58.5 | 59.4 | −1.5 |
| 2 | 133.2 | 129.6 | −2.8 |
| 3 | 159.0 | 153.9 | +2.3 |
| 4 | 469.8 | 452.7 | +3.8 |
| 5 | 190.8 | 195.3 | −2.3 |
| 6 | 261.0 | 269.1 | −3.0 |
| 7 | 292.5 | 287.1 | +1.9 |
| 8 | 175.5 | 180.0 | −2.5 |
| 9 | 333.0 | 324.0 | +2.8 |
| 10 | 648.0 | 675.0 | −4.0 |

The principal properties of the biosensor used in method described above are summarized in Table II

TABLE II

| Temperature of analysis | 37° C. |
|---|---|
| pH | 8.0 |
| Buffer | 0.1 M glycine |
| Response time | 2 minutes |
| Lifetime (expressed as number of tests) | 180–200 |
| Equation of calibration curve: $Y = \Delta i(nA)$; $X = $ [lactic acid] in ppm | $Y = 2.6 + 0.12X$ |
| Linearity range | 5–300 ppm |
| Correlation coefficient | 0.9990 |
| Minimum detection limit | 2.5 ppm |
| Reproducibility of measurements (expressed as "pooled standard deviation" in the linearity range) | 2.8% |

Figure 4:
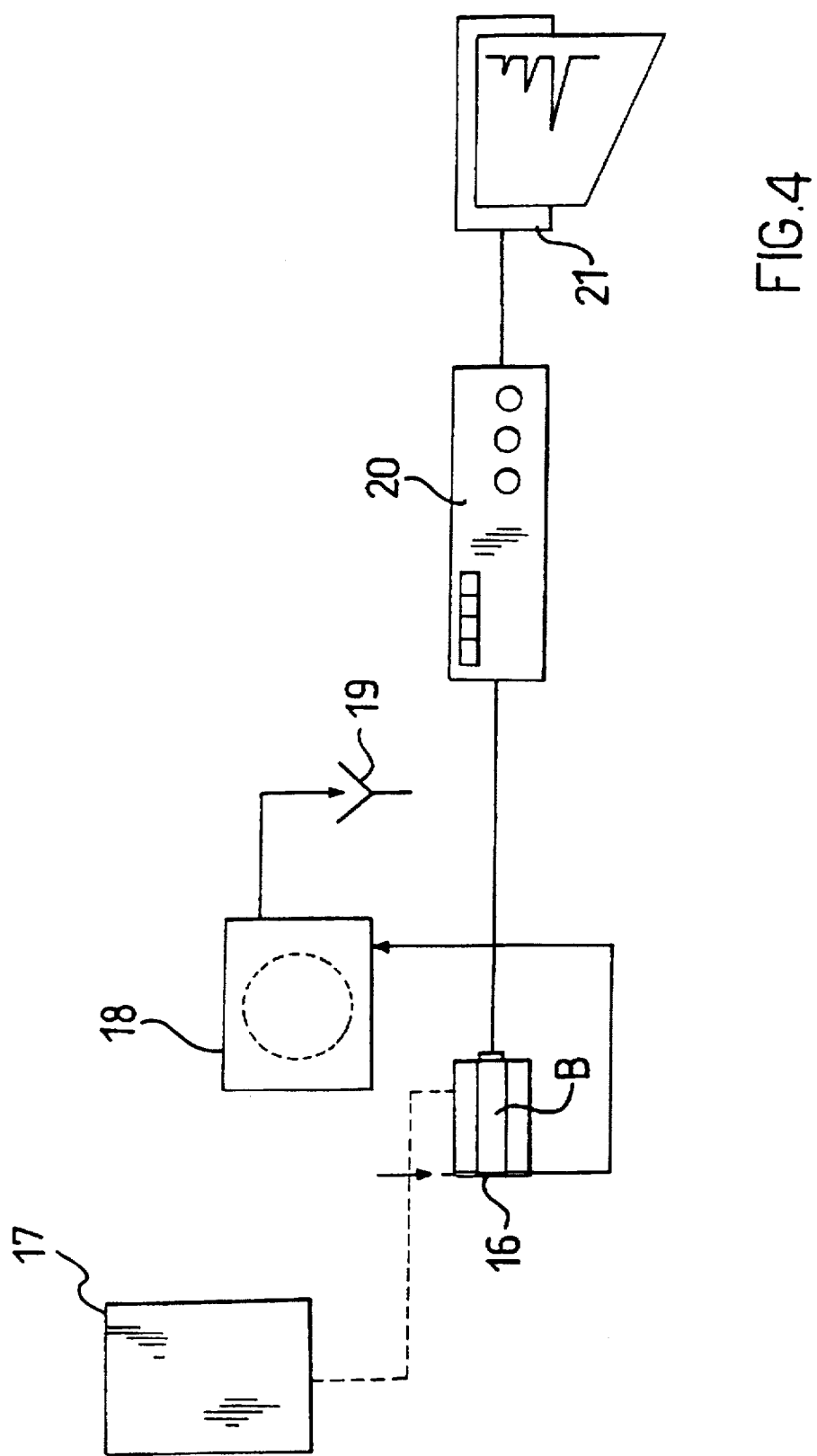
FIG. 4 shows a diagrammatic representation of a variant of the equipment for putting the method according to the invention into effect.

With reference to FIG. 4, alternative equipment for putting the method according to the invention into effect consists of a biosensor B, identical to the one described above, inserted into a flow cell 16, into which the fluid for analysis is fed. The flow cell 16 is kept at a constant temperature by the thermostat 17 and is in fluid contact with a peristaltic pump 18 connected to a outlet 19 for the fluid that has undergone measurement. The electrode of biosensor B is connected to an amperometric measuring device 20, whose output is connected to a chart recorder 21.

According to an alternative embodiment of the invention, the method can be carried out using the equipment described above with reference to FIG. 4.

According to this embodiment, the sample for analysis or the concentrated aqueous extract obtained from it is fed into the flow cell 16, which is kept at a constant temperature by the thermostat 17 and in which is located the biosensor B containing immobilized LOD, D-LDH and HPO. As a result of the reactions catalyzed by these enzymes, oxygen is produced which is detected by biosensor B, producing an electrical signal, which is transmitted to the amperometric measuring device 20 and registered on the chart recorder 21.

The fluid emerging from the flow cell 16 is discharged by means of a peristaltic pump 18 through the outlet 19.

The use of the embodiment of the invention described above enables the analytical method to be automated, thereby reducing the analysis times and simplifying the procedure while maintaining more than satisfactory reproducibility, as demonstrated by the experimental results shown in Table III below, which are the means of at least ten determinations performed on samples of tomato juice.

TABLE III

| Sample No. | Values obtained by the method acc. to the invention using the equipment in FIG. 4 (a) | Values obtained by the enzymatic spectrophotometric method, Boehringer-Mannheim Enzymatic Kit Cat. No. 1112821 (b) | (a − b)/b% |
|---|---|---|---|
| 1 | 105.0 | 112.6 | −6.7 |
| 2 | 51.0 | 52.6 | −3.1 |
| 3 | 94.6 | 99.4 | −4.8 |
| 4 | 120.8 | 122.5 | −1.4 |
| 5 | 57.3 | 59.5 | −3.7 |
| 6 | 152.3 | 165.6 | −8.0 |
| 7 | 63.1 | 66.5 | −7.3 |
| 8 | 86.0 | 92.3 | −6.8 |
| 9 | 132.5 | 145.0 | −8.6 |
| 10 | 210.1 | 225.3 | −7.3 |

The principal properties of the biosensor according to the invention used in the method according to the alternative embodiment described above are summarized in Table IV below.

TABLE IV

| Temperature of analysis | ambient temp. |
|---|---|
| pH | 8.5 |
| Buffer | 0.1 M glycine |
| Response time | 1 minute |
| Lifetime (expressed as number of tests) | 500–600 |
| Equation of calibration curve: $Y = \Delta i(nA)$; $X = $ [lactic acid] in ppm | $Y = 0.33 + 0.056X$ |
| Linearity range | 50–450 ppm |
| Correlation coefficient | 0.9950 |
| Minimum detection limit | 40 ppm |
| Reproducibility of measurements (expressed as "pooled standard deviation" in the linearity range) | 6.0% |

The perfect reproducibility of the method and its excellent accuracy, sensitivity and simplicity make it ideal for a wide variety of applications in the food industry (tomato, fruit juices, prepacked products, canned meats, etc.).

Finally, it should be mentioned that the method according to the invention is easy to perform, even outside a chemical laboratory and even for staff who are not specially trained, thus considerably reducing overall costs.

We claim:

1. A method for the simultaneous determination of D(−) and L(+) lactic acid in organic materials of alimentary interest comprising the steps of:

reacting in a buffered aqueous medium, a sample of said materials, or a solution obtained by extracting these materials with solvent, with an enzyme system comprising L(+) lactate (LOD), D(−) lactate dehydrogenase (D-LDH) and horseradish peroxidase (HPO) in the presence of NAD and $Mn^{++}$, wherein enzymes LOD, D-LDH and HPO are immobilized on least one suitable support, measuring the concentration of any oxygen formed as a result of the oxidation of the lactic acid contained in the sample or the solution with the aid of an amperometric electrode selective for oxygen.

2. The method according to claim 1, wherein said enzymes are immobilized on a single support comprising a membrane.

3. The method according to claim 2, wherein the amperometric electrode used for measurement is separated from the buffered aqueous medium by a first, gas-permeable membrane that is in direct contact with the electrode and wherein a second membrane bearing immobilized enzymes is placed externally over this first membrane.

4. The method according to claim 3, wherein a further membrane, consisting of a dialysis membrane, is placed externally over said second membrane.

5. The method according to claim 4, wherein said second membrane is a membrane made of nylon 6, 6 bearing carboxyl groups on said second membrane surface.

6. The method according to claim 5, wherein the amperometric electrode consists of a platinum wire electrode coated with a layer of an epoxy resin, which separates and insulates said platinum electrode from a Ag/AgCl reference electrode arranged coaxially around said platinum electrode, wherein the two electrodes are fixed inside a cylindrical container filled with an electrolyte solution or an electrolyte gel with a suitable coating interposed, and wherein said platinum electrode acts as an indicator for the oxygen.

7. Method according to claim 6, wherein said platinum electrode is kept at a potential of approximately −650 mV compared with the reference electrode.

8. Method according to claim 1, wherein the amperometric electrode is separated from the buffered aqueous medium by a first membrane made of Teflon, over which are placed externally a second membrane consisting of said membrane made of nylon 6.6 bearing immobilized LOD, D-LDH and HPO and a third membrane consisting of a dialysis membrane.

* * * * *

UNITED STATES PATENT AND TRADEMARK OFFICE
CERTIFICATE OF CORRECTION

PATENT NO. : 5,759,796
DATED : June 2, 1998
INVENTOR(S) : Alfredo Azzoni, Corrado Belicchi, Barbara Cavalieri, Franco Mazzei, Claudio Botre It is certified that error appears in the above-identified patent and that said Letters Patent is hereby corrected as shown below:

On the title page: Item [30] Foreign Application Priority Data:

Foreign Application Priority Data
May 24, 1995    [IT]    Italy ........... MI95 A 001062 --

Signed and Sealed this

Tenth Day of November 1998

*Attest:*

BRUCE LEHMAN

*Attesting Officer*     *Commissioner of Patents and Trademarks*